United States Patent [19]

Kagawa et al.

[11] Patent Number: 5,068,336

[45] Date of Patent: Nov. 26, 1991

[54] PROCESS FOR PRODUCING 2-(4'-HYDROXPHENOXY)-3-CHLORO-5-TRIFLUOROMETHYLPYRIDINE

[75] Inventors: Takumi Kagawa; Takashi Morooka; Kenji Tsuzuki, all of Shinnanyo, Japan

[73] Assignee: Tosoh Corporation, Uchi, Japan

[21] Appl. No.: 484,513

[22] Filed: Feb. 26, 1990

[51] Int. Cl.$^5$ ............... C07D 213/643; C07D 213/64; C07D 213/26
[52] U.S. Cl. .................................. 546/302; 546/345
[58] Field of Search ......................... 546/302

[56] References Cited

U.S. PATENT DOCUMENTS 4,410,701 10/1983 Krauss ............................... 546/302

OTHER PUBLICATIONS

Chemical Abstracts, vol. 95, (15), Abst. No. 132,686–z, Oct. 12, 1981.

Chemical Abstracts, vol. 98, (23), Abst. No. 198,027d, Jun. 6, 1983.

Kitalla, Dimethylformamide Chemical Uses, pp. 6, 8, 33, 36, 60, 90, published by E. I. DuPont de Nemours and Co., 1967 (Wilmington, Del.).

*Primary Examiner*—Alan L. Rotman
*Attorney, Agent, or Firm*—Nixon & Vanderhye

[57] ABSTRACT

A process of producing 2-(4'-hydroxyphenoxy)-3-chloro-5-trifluoromethylpyridine with high efficiency, which is suited for industrial scale production is disclosed. In the process of the present invention, hydroquinone, a dehydrohalogenating agent in the amount of 0.10–0.70 equivalent of the hydroquinone, and a mixed solvent of a polar aprotic solvent and an aromatic hydrocarbon solvent are mixed. The resulting mixture is then heated to reflux at atmospheric pressure to dehydrate the mixture. Then 2,3-dichloro-5-trifluoromethylpyridine in the amount of 0.20–0.95 equivalent of the dehydrohalogenating agent is added to the mixture, and the resulting mixture is allowed to react at a temperature of 100°–170° C.

7 Claims, No Drawings

PROCESS FOR PRODUCING 2-(4'-HYDROXPHENOXY)-3-CHLORO-5-TRIFLUOROMETHYLPYRIDINE

BACKGROUND OF THE INVENTION

I. Field of the Invention

This invention relates to a process of producing 2-(4'-hydroxyphenoxy)-3-chloro-5-trifluoromethylpyridine. 2-(4'-hydroxyphenoxy)-3-chloro-5-trifluoromethylpyridine is an important compound as an intermediate in the production of pharmaceuticals and agricultural chemicals.

II. Description of the Related Art

A process of producing 2-(4'-hydroxyphenoxy)-3-chloro-5-trifluoromethylpyridine is known in which hydroquinone, 2,3-dichloro-5-trifluoromethylpyridine and potassium hydroxide are reacted in dimethylsulfoxide as a solvent under nitrogen atmosphere under stirring at 150° C. for 2 hours, the resulting mixture is allowed to cool and neutralized with hydrochloric acid, the resultant is extracted with methylene chloride, and the obtained extract is dried and condensed to obtain the desired product (Japanese Laid Open Patent Application (Kokai) No. 61182/79).

However, in this process, the yield of the product is low because of the influence of water produced as a byproduct by the reaction of hydroquinone and potassium hydroxide. Further, the operations for carrying out the process are complicated. Thus, although this process may be suited for the production in laboratory scale, it is not suited for industrial scale production.

Also known is a process of producing 2-(4'-hydroxyphenoxy)-3-chloro-5-trifluoromethylpyridine in which hydroquinone is dissolved in a polar solvent, the obtained solution is degassed under heat under low vacuum, aqueous sodium hydroxide or potassium hydroxide is added to the solution in the amount sufficient to neutralize 75 -100% of hydroquinone, the resulting mixture is heated under low vacuum so as to distill water until the residual water content is reduced to not more than 1% by weight of the solvent and the reactants, the vacuum is released with a dry inert gas, and the resultant is cooled and reacted with 2,3-dichloro-5-trifluoromethylpyridine to obtain the desired product with high yield (Japanese Laid Open Patent Application (Kokai) No. 962/83).

However, in this method, removal of the water dissolved in the polar aprotic solvent and the water produced as a byproduct is extremely difficult, so that complicated operations are necessary to reduce the water content to the level not adversely affecting the reaction. Further, it is necessary to distill off water under low vacuum, which is troublesome.

Still another process of producing 2-(4'-hydroxyphenoxy)-3-chloro-5-trifluoromethylpyridine is known, in which 2,3-dichloro-5-trifluoromethylpyridine and 4-methoxyphenol are reacted in dimethylsulfoxide at 80°-85° C. and the obtained 2-(4'-methoxyphenoxy)-3-chloro-5-trifluoromethylpyridine is demethylated with 48% aqueous hydrobromic acid solution t obtain the desired product (Japanese Patent Publication (Kokoku) No. 44747/88).

However, this process cannot be carried out in one pot, so that it is not suited for industrial scale production.

SUMMARY OF THE INVENTION

Accordingly, the object of the present invention is to provide a process of producing 2-(4'-hydroxyphenoxy)-3-chloro-5-trifluoromethylpyridine with high efficiency by simple operations, which is suited for industrial scale production.

The present inventors intensively studied to find that the water contained in polar aprotic solvent and the water produced as a byproduct by a reaction between hydroquinone and a dehydrohalogenating agent can easily be removed by heating to reflux the mixture at atmospheric pressure by employing a mixed solvent of a polar aprotic solvent and an aromatic hydrocarbon solvent, that no adverse effect is brought about by employing the mixed solvent, and that 2-(4'-hydroxyphenoxy)-3-chloro-5-trifluoromethylpyridine can be obtained with high yield and at high purity, to complete the present invention.

That is, the present invention provides a process of producing 2-(4'-hydroxyphenoxy)-3-chloro-5-trifluoromethylpyridine comprising the steps of mixing hydroquinone, a dehydrohalogenating agent in the amount of 0.10-0.70 equivalent to the hydroquinone, and a mixed solvent of a polar aprotic solvent and an aromatic hydrocarbon solvent; heating to reflux the resulting mixture at atmospheric pressure to remove the water from the reaction mixture; adding to the resulting mixture 2,3-dichloro-5-trifluoromethylpyridine in the amount of 0.20-0.95 equivalent to the dehydrohalogenating agent; and reacting the resulting mixture at 100°-170° C.

By the process of the present invention, 2-(4'-hydroxyphenoxy)-3-chloro-5-trifluoromethylpyridine can be produced with high yield and the process may be carried out by simple operations in one pot. Thus, the process of the present invention is suited for industrial production.

DETAILED DESCRIPTION OF THE PREFERRED EMBODIMENTS

In the first step of the process of the present invention, hydroquinone, dehydrohalogenating agent, a polar aprotic solvent and an aromatic hydrocarbon solvent are mixed.

Preferred examples of the polar aprotic solvent used herein may include N,N-dimethylformamide, N,N-dimethylacetamide, dimethylsulfoxide, hexamethylphosphortriamide and N-methylpyrrolidone. Among these, in view of the stability and ease of handling, dimethylsulfoxide is most preferred.

The aromatic hydrocarbon solvent preferably has a boiling point of not lower than 100° C. because removal of water may easily be carried out by heating to reflux under atmospheric pressure. Preferred examples of the aromatic hydrocarbon solvent may include benzene, toluene, xylene, ethylbenzene, cumene and mesitylene.

Although wide range of mixing ratio of the polar aprotic solvent and the aromatic hydrocarbon solvent may be employed, if the concentration of the polar aprotic solvent is very high, removal of water takes a long time and may not be completed. On the other hand, if the concentration of the polar aprotic solvent is very low, a large amount of a salt compound of hydroquinone is precipitated by the reaction between the dehydrohalogenating agent and hydroquinone, so that the reaction rate of the subsequent reaction with 2,3-dichloro-5-trifluoromethylpyridine may be lowered.

Thus, the mixing ratio of the polar aprotic solvent to the aromatic hydrocarbon solvent may preferably be 95:5–20:80 by weight.

If the concentration of hydroquinone in the mixed solvent is not higher than 0.5% by weight, the solvent is too excess to complete the reaction from the view point of economy, and if it is not lower than 30% by weight, a large number of the salt compound of hydroquinone is precipitated, so that the reaction rate of the subsequent reaction with 2,3-dichloro-5-trifluoromethylpyridine may be lowered. Thus, the concentration of hydroquinone in the mixed solvent may preferably be 0.5–30% by weight.

Preferred examples of the dehydrohalogenating agent may include alkali metals hydroxides and alkaline earth metals hydroxides such as lithium hydroxide, sodium hydroxide, potassium hydroxide, rubidium hydroxide, cesium hydroxide, beryllium hydroxide, magnesium hydroxide, potassium hydroxide, strontium hydroxide; alkali metals and alkaline earth metals carbonates such as lithium carbonate, sodium carbonate, potassium carbonate, rubidium carbonate, cesium carbonate, beryllium carbonate, magnesium carbonate, potassium carbonate and strontium carbonate; and alkali metals hydrogen carbonates such as lithium hydrogen carbonate, sodium hydrogen carbonate, potassium hydrogen carbonate, rubidium hydrogen carbonate and cesium hydrogen carbonate. Among these, in view of the economy and of solubility of the produced salt compound in the reaction medium, sodium hydroxide, potassium hydroxide, sodium carbonate, potassium carbonate, sodium hydrogen carbonate and potassium hydrogen carbonate are preferred.

The amount of the dehydrohalogenating agent is 0.10–0.70 equivalent to hydroquinone. If the amount is less than 0.10 equivalent, it is not economic because unnecessarily excess hydroquinone exists in the reaction system, while if the amount is more than 0.70 equivalent, the yield of the desired product may be lowered because of a side reaction.

The dehydrogen halide may be added in the form of solid or in the form of an aqueous solution.

In the second step, the reaction mixture is dehydrated. The removal of water from the reaction mixture containing the salt compound of hydroquinone produced by the reaction between the dehydrohalogenating agent and hydroquinone may be carried out by heating the mixture to a temperature at which the aromatic hydrocarbon solvent refluxes under atmospheric pressure, and water is also distilled azeotropically with the aromatic hydrocarbon solvent.

Although the duration of the dehydration of the reaction mixture varies depending on the employed dehydrogen halide, the polar aprotic solvent, and the aromatic hydrocarbon solvent as well as the mixing ratio of the polar aprotic solvent and the aromatic hydrocarbon solvent, and on the state of reflux by heating, the removal of the water usually completes in 10 hours.

In the third step, 2,3-dichloro-5-trifluoromethylpyridine is added to the resulting mixture.

The amount of 2,3-dichloro-5-trifluoromethylpyridine is 0.20–0.95 equivalent to the dehydrohalogenating agent. If the amount is more than 0.95 equivalent, the yield of the desired product based on the amount of 2,3-dichloro-5-trifluoromethylpyridine is reduced. On the other hand, an amount of less than 0.20 equivalent is not preferred because of the economy and the yield is not increased by employing such a small amount. In a preferred mode of the present invention especially suited for industrial scale production, the amount of 2,3-dichloro-5-trifluoromethylpyridine is not more than 0.95 mole with respect to one mole of hydroquinone in view of the production yield.

2,3-Dichloro-5-trifluoromethylpyridine may be added at a temperature from room temperature to 170° C.

In the fourth step, the salt compound of hydroquinone and 2,3-dichloro-5-trifluoromethylpyridine are allowed to react at a temperature of 100°–170° C. If the reaction temperature is lower than 100° C., it takes a long time to complete the reaction. On the other hand, if the reaction temperature is higher than 170° C., side reaction may occur so that the yield of the desired product based on 2,3-dichloro-5-trifluoromethylpyridine may be lowered.

The reaction time after the addition of 2,3-dichloro-5-trifluoromethylpyridine at a temperature within the above-described range is usually 2–20 hours.

By the above-described steps, the desired 2-(4'-hydroxyphenoxy)-3-chloro-5-trifluoromethylpyridine may be produced.

In a preferred mode of the present invention, which is especially suited for the production in an industrial scale, the process further comprises the subsequent steps as follows:

That is, in the fifth step, the reaction mixture is cooled to a temperature of not higher than 100° C. and hydrogen chloride or hydrochloric acid is added to the reaction mixture so as to neutralize the excess dehydrohalogenating agent.

Although one equivalent of hydrogen chloride or hydrochloric acid with respect to the residual dehydrohalogenating agent is sufficient in theory, if the amount of hydrogen chloride or hydrochloric acid is smaller than a certain level, a salt of the desired 2-(4'-hydroxyphenoxy)-3-chloro-5-trifluoromethylpyridine may remain and not extracted by the subsequent extraction with hot aliphatic hydrocarbon solvent, so that the yield of the desired product may be reduced. On the other hand, use of a much excess hydrogen chloride or hydrochloric acid does not give any additional benefit. Thus, the amount of hydrogen chloride or hydrochloric acid may preferably be 1.1–5.0 moles per one mole of the excess dehydrohalogenating agent.

In cases where hydrochloric acid is used, if the hydrochloric acid is too dilute, a large volume of hydrochloric acid is required and if it is too concentrated, it smokes at the time of addition, so that the ease of handling is degraded. Thus, the concentration of hydrochloric acid may usually be 1–36% by weight, preferably be 5–25% by weight.

The addition of hydrogen chloride or hydrochloric acid may be carried out at a temperature not higher than 100° C. without problem.

In the next step, the solvent of the reaction mixture is removed by distillation. In case where hydrogen chloride is used for neutralizing the excess amount of dehydrogen halide, the distillation can be carried out at a temperature of not higher than 200° C. without problem. In cases where hydrochloric acid is used for the neutralization, the desired product may be decomposed at a temperature of higher than 120° C., so that the distillation is carried out at a reduced pressure at not higher than 120° C.

By distilling off the solvent, a black viscous oil containing an inorganic salt may be remained.

In the next step, the thus obtained residue is extracted with an aliphatic hydrocarbon solvent. Any aliphatic hydrocarbon solvent which is available in industrial scale may preferably be employed, and examples thereof include pentane, hexane, benzine and ligroin.

Although the amount of the aliphatic hydrocarbon solvent varies depending on the solvent used, the total amount of the solvent may usually be 10-300 times the content of the desired product.

The extraction may be carried out by batch process or by continuous process. In cases where the extraction is carried out by batch process, the extraction may preferably be carried out 3-10 times.

Although the extraction may be carried out at a temperature not higher than the boiling point of the solvent, if the temperature of the solvent is lower than 35° C., the solubility of the desired product in the solvent is sharply decreased. Therefore, the extraction may preferably be carried out at a temperature of not lower than 35° C. and not higher than the boiling point of the solvent.

By removal of solvent from the extract, the desired 2-(4'-hydroxyphenoxy)-3-chloro-5-trifluoromethylpyridine may be obtained in the form of a white to light yellow solid.

The present invention will now be described by way of examples thereof. It should be noted that the examples are presented for the illustration purpose only and should not be interpreted in any restrictive way.

EXAMPLE 1

To a 200 ml three-necked round flask equipped with a condenser, water separator and a 10 ml dropping funnel, 3.30 g of hydroquinone and 1.52 g of solid potassium carbonate were placed and the atmosphere was replaced with nitrogen. Then 50 g of dimethylsulfoxide and 50 g of m-xylene were added. The flask was placed in an oil bath and the temperature of the oil bath was raised to 150° C. so as to reflux the mixture. The distilling out of water observed by gross observation ended after two hours from initiation of the reflux and then the reflux was continued for additional two hours.

After cooling the dehydrated reaction mixture to room temperature, 4.37 g of 2,3-dichloro-5-trifluoromethylpyridine was added dropwise from the dropping funnel for 30 minutes. The oil bath was again heated to 150° C. and was kept at this temperature for 3.5 hours under refluxing condition to carry out the reaction. The temperature of the reaction mixture in the flask was 142° C.

After completion of the reaction, the solvent was removed under reduced pressure and the resultant was cooled to room temperature. To the residue, 100 ml of 1N hydrochloric acid was added and the resultant was extracted three times with 50 ml each of diethyl ether. The extract was dried over sodium sulfate and was concentrated to obtain 6.21 g of a reddish brown viscous oil. By analyzing the oil by gas chromatography, it was proved that 5.56 g of 2-(4'-hydroxyphenoxy)-3-chloro-5-trifluoromethylpyridine was obtained and the yield based on 2,3-dichloro-5-trifluoromethylpyridine was 94.9%.

EXAMPLE 2

In the same apparatus as used in Example 1, 3.31 g of hydroquinone was supplied and the atmosphere was replaced with nitrogen. Then 3.45 of 48% aqueous sodium hydroxide solution, 25 g of mesitylene and 40 g of N,N-dimethylsulfoxide were added to the flask. The flask was placed in an oil bath and the reaction mixture was heated while stirring the mixture. When the temperature of the oil bath reached to 180° C., reflux started and the oil bath was kept at this temperature for 2 hours to carry out the dehydration.

After the completion of the dehydration, the oil bath was cooled to 140° C. and 4.97 g of 2,3-dichloro-5-trifluoromethylpyridine wa added to the mixture. The oil bath was then heated to 170° C. and the reaction was carried out at this temperature for 1 hour. The temperature of the reaction mixture in the flask was 168° C.

The resulting reaction mixture was processed in the same manner as in Example 1 to obtain 6.81 g of a reddish brown viscous oil. Analysis by gas chromatography revealed that 6.46 g of 2-(4'-hydroxyphenoxy)-3-chloro-5-trifluoromethylpyridine was obtained with a yield of 96.9% based on 2,3-dichloro-5-trifluoromethylpyridine.

EXAMPLE 3

In the same apparatus as used in Example 1, 35.18 g of hydroquinone and 17.93 g of solid potassium hydroxide were added and the atmosphere in the flask was replaced with nitrogen. Then 15 g of toluene and 70 g of hexamethylphosphortriamide were added to the flask and the flask was heated in an oil bath while stirring the mixture. When the temperature of the oil bath reached to 140° C., the mixture started to reflux and the oil bath was kept at this temperature for 5 hours to carry out the dehydration. Then 20.70 g of 2,3-dichloro-5-trifluoromethylpyridine was added dropwise the mixture at this temperature without cooling the mixture from the dropping funnel for one hour. The reaction was carried out under reflux condition for 6 hours. The temperature of the reaction mixture in the flask was 115° C.

The resulting reaction mixture was processed in the same manner as in Example 1 to obtain 35.45 g of a reddish oil. Analysis by gas chromatography revealed that 25.95 g of 2-(4'-hydroxyphenoxy)-3-chloro-5-trifluoromethylpyridine was obtained with a yield of 93.5% based on 2,3-dichloro-5-trifluoromethylpyridine.

COMPARATIVE EXAMPLE 1

In the same apparatus as used in Example 1, 3.50 g of hydroquinone, 1.55 g of solid potassium carbonate, and 4.30 g of 2,3-dichloro-5-trifluoromethylpyridine and 100 g of N,N-dimethylsulfoxide were placed and the mixture was heated at 142° C. for 3.5 hours under nitrogen atmosphere.

The resulting reaction mixture was processed in the same manner as in Example 1 to obtain 5.90 g of a reddish oil. Analysis by gas chromatography revealed that 4.73 g of 2-(4'-hydroxyphenoxy)-3-chloro-5-trifluoromethylpyridine was obtained with a yield of 82.0% based on 2,3-dichloro-5-trifluoromethylpyridine.

COMPARATIVE EXAMPLE 2

In the same apparatus as used in Example 1, 3,30 g of hydroquinone, 1.52 g of solid potassium carbonate and 150 g of N,N-dimethylsulfoxide were placed and the mixture was heated to 130° C. The pressure in the flask was reduced by using an aspirator and 50 ml of the water produced as a byproduct and the solvent were removed for 4 hours. After cooling the mixture to room temperature, 4.08 g of 2,3-dichloro-5-trifluoromethylpyridine was added and the mixture was again heated to 142° C. and was kept at this temperature for 3.5 hours to carry out the reaction.

The resulting reaction mixture was processed in the same manner as in Example 1 to obtain 5.90 g of a reddish oil. Analysis by gas chromatography revealed that 4.82 g of 2-(4'-hydroxyphenoxy)-3-chloro-5-trifluoromethylpyridine was obtained with a yield of 88.1% based on 2,3-dichloro-5-trifluoromethylpyridine.

EXAMPLE 4

In a 300 ml three-necked round flask equipped with a stirrer and a water separator with a Liebig's condenser, 2.99 g of hydroquinone, 1.37 g of potassium hydroxide, 15 g of dimethylsulfoxide and 15 g of toluene were placed and the flask was heated in an oil bath while stirring the mixture. When the temperature of the mixture in the flask reached to 100° C., the toluene started to reflux and the dehydration was initiated.

After three hours from the initiation of the reflux, the dehydration ended judging from the gross observation, but the reflux was continued for another 2 hours.

The obtained solution of a salt of hydroquinone was cooled to 40° C. under stirring and then 5.00 g of 2,3-dichloro-5-trifluoromethylpyridine was added dropwise thereon for 0.5 hours. The resulting mixture was heated to 110° C. and reaction was carried out under refluxing conditions for 8.0 hours.

After completion of the reaction, the mixture was cooled to 100° C. and 0.06 g (36.8 ml at 0° C.) of hydrogen chloride gas was bubbled in the mixture for 30 minutes to neutralize the excess base. Then an apparatus for distillation under reduced pressure was equipped to the flask and the solvent was distilled off under reduced pressure for 2 hours to obtain a black viscous oil.

After cooling the thus obtained oil to 59° C., 300 g of hexane was added at 59° C. and the mixture was stirred. The mixture was then left to stand for 5 minutes at this temperature and the hexane layer was collected by decantation. The remainder was extracted three times with 300 g each of hexane, and the hexane layers were combined and concentrated to obtain 64.2 g of light yellow solid.

Analysis by gas chromatography revealed that the conversion rate of 2,3-dichloro-5-trifluoromethylpyridine was 99%, the purity of the product was 98% and the yield of the product was 94%.

EXAMPLES 5-8

Using an apparatus similar to that used in Example 4, the reactions were carried out under the conditions set forth in Table 1 below. In Example 5 and 6, a 300 ml reaction vessel was used and in Example 8, a 2000 ml reaction vessel was used. In Example 7, the reaction was carried out in a 300 ml reaction vessel and the extraction was carried out in a 1000 ml reaction vessel.

The results are shown in Table 1.

COMPARATIVE EXAMPLE 3

Using a 1000 ml reaction vessel and dimethylsulfoxide alone as the solvent, the reaction was carried out in the similar manner to Example 4 under the conditions shown in Table 1. In the dehydration step, 470 g of dimethylsulfoxide was distilled off under reduced pressure. The results are shown in Table 1.

COMPARATIVE EXAMPLES 4 AND 5

Using the same apparatus as used in Example 4, the reaction was carried out under the conditions shown in Table 1. The results are shown in Table 1.

TABLE 1

| | TFDCP 1) g (mmol) | HQ 2) g (mmol) | Dehydrohalogenating Agent Amount used (g) | Aprotic Solvent Amount Used (g) | Aromatic Hydrocarbon Solvent Amount Used (g) | Dehydration Temp. × Time °C. × hr | TFDCP Dropping °C. × hr | Aging °C. × hr |
|---|---|---|---|---|---|---|---|---|
| Example 4 | 5.00 (23.15) | 2.99 (27.15) | KOH 1.37 (24.42) | DMSO 15 | Toluene 15 | 110 × 5.0 | 40 × 0.5 | 110 × 8.0 |
| Example 5 | 10.20 (47.22) | 33.03 (299.97) | NaOH 3.78 (94.50) | DMF 102 | Ethylbenzene 8 | 136 × 4.0 | 136 × 2.0 | 136 × 4.0 |
| Example 6 | 7.50 (34.72) | 19.88 (180.55) | K₂CO₃ 9.60 (69.46) | NMP 80 | Xylene 20 | 140 × 4.5 | 30 × 0.1 | 110 × 12.0 |
| Example 7 | 12.80 (59.26) | 9.91 (90.00) | Na₂CO₃ 5.23 (49.35) | DMAc 36 | Mesitylene 9 | 164 × 2.0 | 100 × 1.0 | 164 × 3.0 |
| Example 8 | 16.30 (75.47) | 8.75 (79.47) | KHCO₃ 10.66 (106.48) | DMSO 300 | Cumene 700 | 176 × 1.0 | 162 × 0.5 | 162 × 2.0 |
| Comparative Example 3 3) | 5.00 (23.15) | 2.99 (27.15) | KOH 1.37 (24.42) | DMSO 500 | — | 110 × 5.0 | 40 × 0.5 | 110 × 8.0 |
| Comparative Example 4 | 5.00 (23.15) | 3.00 (27.25) | KOH 2.74 (48.83) | DMSO 20 | Toluene 20 | 110 × 5.0 | 40 × 0.5 | 110 × 8.0 |
| Comparative Example 5 | 5.00 (23.15) | 3.00 (27.25) | KOH 1.37 (24.42) | DMSO 20 | Cumene 20 | 176 × 1.0 | 40 × 0.5 | 176 × 2.0 |

| | Amount of Added HCl g | Temp. of HCl Added °C. | Distillation off of Solvent °C. × hr | Aliphatic Hydrocarbon Solvent Amount Used (ml) × Times | Extraction Temp. °C. | Yield g | Yield % | Conversion Rate % | Purity % |
|---|---|---|---|---|---|---|---|---|---|
| Example 4 | HCl gas 0.06 | 100 | 110 × 2.0 | Hexane 300 × 4 | 59 | 6.42 | 94 | 99 | 98 |
| Example 5 | Aqueous 25% | 95 | 115 × 2.0 | Benzine | 60 | 13.40 | 95 | 100 | 97 |

TABLE 1-continued

|  |  |  |  |  |  |  |  |  |  |
|---|---|---|---|---|---|---|---|---|---|
|  | HCl Solution 31.02 |  |  |  | 100 × 6 |  |  |  |  |
| Example 6 | HCl gas 18.62 | 100 | 170 × 1.0 | Lygloin 200 × 5 | 120 | 9.54 | 93 | 99 | 98 |
| Example 7 | Aqueous 6% HCl Solution 38.35 | 25 | 100 × 5.0 | Pentane 500 × 6 | 35 | 15.95 | 92 | 98 | 99 |
| Example 8 | Aqueous 15% HCl Solution 15.00 | 60 | 100 × 6.0 | Cyclohexane 40 × 6 | 55 | 22.57 | 96 | 99 | 93 |
| Comparative Example 3 3) | HCl gas 0.06 | 100 | 110 × 2.0 | Hexane 300 × 4 | 59 | 6.07 | 88 | 99 | 97 |
| Comparative Example 4 | HCl gas 1.22 | 100 | 110 × 2.0 | Hexane 300 × 4 | 30 | 4.73 | 65 | 100 | 92 |
| Comparative Example 5 | HCl gas 0.06 | 100 | 110 × 2.0 | Hexane 300 × 4 | 59 | 6.03 | 82 | 99 | 91 |

1) TFDCP: 2,3-dichloro-5-trifluoromethylpyridine.
2) HQ: hydroquinone
3) DMSO alone was used as the solvent and 470 g of DMSO was distilled off in dehydration step.
4) DMSO: dimethylsulfoxide, DMF: N,N-dimethylformamide, NMP: N-methylpyrrolidone, DMAc: N,N-dimethylacetamide.

Although the invention was described by way of preferred examples thereof, it is apparent for those skilled in the art that various modification may be made without departing from the spirit and scope of the present invention.

We claim:

1. A process for producing 2-(4'-hydroxyphenoxy)-3chloro-5-trifluoromethylpyridine comprising the steps of:
   mixing hydroquinone, a dehydrohalogenating agent in the amount of 0.10–0.70 equivalent to the hydroquinone, and a mixed solvent of a polar aprotic solvent and an aromatic hydrocarbon solvent;
   heating to reflux the resulting mixture at atmospheric pressure to dehydrate the mixture;
   adding to the resulting mixture 2,3-dichloro-5-trifluoromethylpyridine in the amount of 0.20–0.95 equivalent to the dehydrohalogenating agent; and reacting the resulting mixture at 100°–170° C.

2. A process of producing 2-(4'-hydroxyphenoxy)-3-chloro-5-trifluoromethylpyridine, wherein the amount of 2,3-dichloro-5-trifluoromethylpyridine is not more than 0.95 mole per one mole of hydroquinone, the process further comprising the steps of:
   adding hydrogen chloride or hydrochloric acid to the mixture after said reaction at 100°–170° C.;
   distilling off said mixed solvent to obtain a residue; and
   extracting said residue with an aliphatic hydrocarbon solvent at a temperature of not lower than 35° C. and not higher than its boiling point.

3. The process of claim 1, wherein said polar aprotic solvent is N,N-dimethylformamide, N,N-dimethylacetamide, dimethylsulfoxide, hexamethylphosphortriamide or N-methylpyrrolidone.

4. The process of claim 1, wherein said aromatic hydrocarbon solvent is benzene, toluene, xylene, ethylbenzene, cumene or mesitylene.

5. The process of claim 1, wherein the mixing ratio of said polar aprotic solvent to said aromatic hydrocarbon solvent is 95:5–20:80 by weight.

6. The process of claim 1, wherein the dehydrohalogenating agent is alkali metals hydroxides, alkaline earth metals hydroxides, alkali metals carbonates, alkaline earth metals carbonates or alkali metals hydrogen carbonates.

7. The process of claim 2, wherein the amount of said hydrogen chloride or hydrochloric acid is 1.1–5.0 moles per one mole of said dehydrohalogenating agent.

* * * * *